United States Patent [19]

Pyke

[11] Patent Number: 4,671,852
[45] Date of Patent: Jun. 9, 1987

[54] METHOD OF FORMING SUSPENDED GATE, CHEMICALLY SENSITIVE FIELD-EFFECT TRANSISTOR

[75] Inventor: Stephen C. Pyke, Willowick, Ohio

[73] Assignee: The Standard Oil Company, Cleveland, Ohio

[21] Appl. No.: 860,722

[22] Filed: May 7, 1986

[51] Int. Cl.$^4$ .............. C23F 1/02; B44C 1/22; C03C 15/00; C03C 25/06
[52] U.S. Cl. .................... 156/652; 156/643; 156/644; 156/656; 156/659.1; 29/571; 204/1 T; 204/416; 252/79.5; 324/71.5; 340/634; 357/25; 357/41
[58] Field of Search .............. 252/79.5, 79.2, 643; 156/644, 652, 656, 659.1; 204/1 T, 416, 192 EC, 192 E; 340/634; 29/571; 357/23.1, 41, 25; 324/71.5

[56] References Cited

U.S. PATENT DOCUMENTS

| | | | |
|---|---|---|---|
| 4,411,741 | 10/1983 | Janata | 204/1 T |
| 4,456,522 | 6/1984 | Blackburn | 204/416 |
| 4,486,292 | 12/1984 | Blackburn | 204/416 |
| 4,514,263 | 4/1985 | Janata | 204/1 T |

OTHER PUBLICATIONS

Wolters et al., "Properties of Reactive Sputtered TiW", Solid State Technology, Feb. 1986, pp. 131–136.

*Primary Examiner*—William A. Powell
*Attorney, Agent, or Firm*—Joseph G. Curatolo; Larry W. Evans

[57] ABSTRACT

A method is disclosed for forming a chemically sensitive field-effect transistor having a suspended gate which enables the uniform and reproducible manufacture of such devices. Controlled uniformity and device response is provided by this method which makes the field-effect transistors suitable for use as sensors, alarms and analyzers for gases. A method of regenerating a chemically sensitive field-effect transistor having a suspended gate is also disclosed.

18 Claims, 5 Drawing Figures

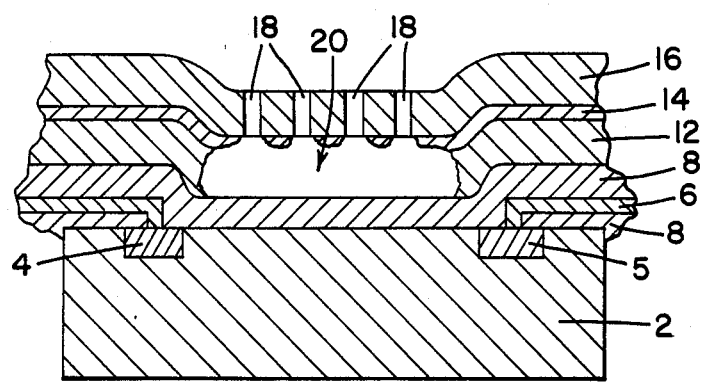
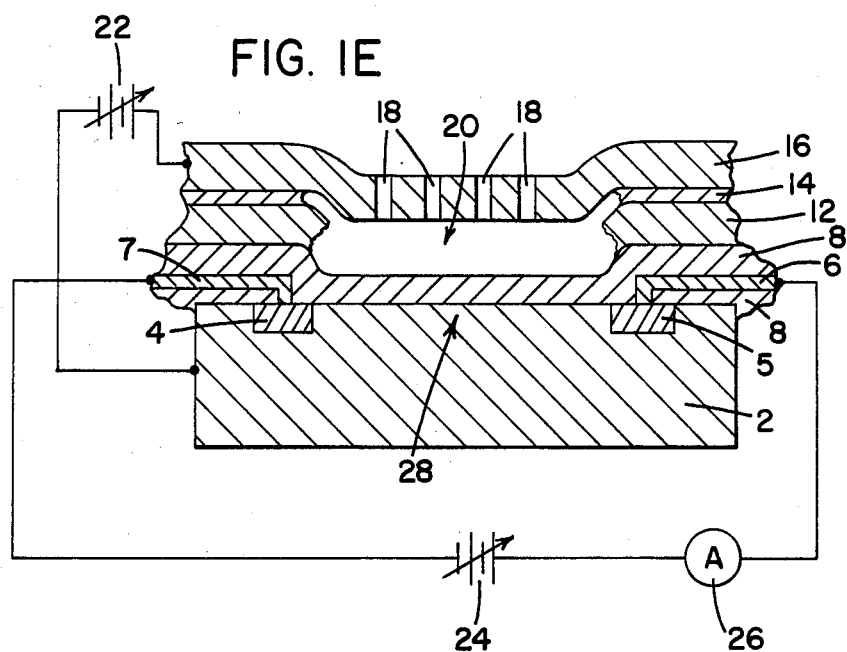

METHOD OF FORMING SUSPENDED GATE, CHEMICALLY SENSITIVE FIELD-EFFECT TRANSISTOR

FIELD OF THE INVENTION

The present invention relates to a method of forming a suspended gate chemically sensitive field-effect transistor (SGFET). The method taught herein provides stable, reproduceable SGFETs that are useful for detecting specific components in a liquid or gaseous fluid.

BACKGROUND OF THE INVENTION

Chemically sensitive field-effect transistors (CHEMFETs) have been developed for the detection of specific compounds in liquid and gaseous environments. Originally, these CHEMFETs were ion sensitive, as disclosed in U.S. Pat. No. 4,020,830 to Johnson et al. entitled "Selective Chemical Sensitive FET Transducers" and by Piet Bergveld, "Development, Operation, and Application of the Ion-Sensitive-Field-Effect Transistor as a Tool for Electrophysiology", IEEE Transactions of Biomedical Engineering, pages 342-351, September, 1972.

Other developments produced CHEMFETs specifically capable of measuring the concentrations of components in a gaseous state, as for example the device disclosed in U.S. Pat. No. 3,719,564 to Lilly, Jr. et al.; the device described by Lundstrom in "A Hydrogen-Sensitive MOS Field-Effecting Transistor", 26 Applied Physics Letters, pages 55-57, Jan. 15, 1975; and the device described by G. Phillips entitled "An Electronic Method of Detecting Impurities In The Air", Volume 28, Journal of Scientific Instrumentation, pages 342-347, 1951.

A further advancement occurred with the disclosure of suspended gate field-effect transistors by Jiri Janata in U.S. Pat. Nos. 4,411,741 and 4,514,263, both of which patents are incorporated herein by reference. These patents describe an apparatus and method for measuring the concentration of various components in a liquid or gaseous fluid sample. The apparatus comprises a chemically sensitive field-effect transistor having a semiconductor substrate and a pair of diffusion regions formed at the surface of the substrate. An electrical insulating layer is positioned adjacent the substrate and a fluid pervious gate member is mounted to the insulating layer so as to form a gap between the suspended gate and insulating layer. The apparatus also includes means for imposing an electrical charge on the suspended gate, means for imposing an electrical potential between the diffusion regions, and means for detecting current flow between the diffusion regions. The fluid sample to be analyzed is introduced through the suspended gate and into the gap where various components of the fluid sample are adsorbed by the suspended gate, and in another embodiment, also by an adsorptive layer which is applied within the gap. The suspended gate and the adsorbtive layer can be specifically chosen so as to render the apparatus chemically selective to one or more specific fluid components.

The suspended gate field-effect transistor described by Janata above may provide a route to novel gas detection devices such as the miniature and portable gas detection device described in U.S. Ser. No. 811,548, filed Dec. 20, 1985, entitled "Method and Device for Detection of Changes in Gas Concentration". However, it has been found that the characteristics of suspended gate field-effect transistors having noble metal suspended gates are quite irregular and vary widely from SGFET to SGFET. The same suspended gate field-effect transistor may not be capable of reproducible sensing, and the responses from SGFET to SGFET may vary in an unpredictable manner. Such variation makes suspended gate field-effect transistors unsuitable for use as gas detection devices. What is needed is a method of forming suspended gate field-effect transistors having stable and uniform gas detection characteristics.

Thus, it is an object of the present invention to provide a method for forming suspended gate field-effect transistors having desirable gas detection characteristics and substantially uniform sensitivities from SGFET to SGFET.

It is another object of the present invention to provide a method of regenerating a chemically sensitive field-effect transistor having a suspended gate.

These and other objects of the present invention will become apparent to one skilled in the art from the below description of the invention and the appended claims.

SUMMARY OF THE INVENTION

The present invention relates to a method of forming a chemically sensitive field-effect transistor having a suspended gate which method comprises:

- providing a p-type silicon substrate having two spaced-apart diffusion regions of n-type doping polarity on the surface thereof;
- providing external electrical contacts to each diffusion region;
- depositing an electrically insulating layer onto the substrate and electrical contacts;
- depositing a fugitive layer containing a material selected from the group of aluminum and silicon onto the electrically insulating layer;
- forming a thin film on the fugitive layer which contains at least one element selected from the group of refractory and transition metals;
- depositing a noble metal gate material onto the thin film;
- forming holes through said noble metal and thin film layers so as to form a gridded area between said diffusion regions;
- removing the fugitive layer disposed under the gridded surface; and
- etching with a buffered solution containing a complexing agent for aqueous metal ions to remove the thin film under the gridded area, and so form a suspended gate field-effect transistor having a noble metal gate.

The present invention also relates to a method of regenerating a chemically sensitive field-effect transistor having a suspended gate, which method comprises disposing the suspended gate in contact with a buffered solution containing a complexing agent for aqueous metal ions so as to remove any metal contaminants adhering to the suspended gate.

DETAILED DESCRIPTION OF THE INVENTION

In accordance with the present invention there are provided methods for forming and regenerating a chemically sensitive field-effect transistor having a suspended gate that is essentially free of any material other than the suspended gate material, so as to have a well-defined chemical sensitivity that may be uniformly reproduced from SGFET to SGFET. This defined chemical sensitivity is especially desirable for the detection of specific components in gaseous states. Uniform reproducibility of the chemically sensitive response is a necessary prerequisite for use of such SGFETs as gas detectors, alarms, analyzers and the like.

The process herein described produces a chemically sensitive field-effect transistor formed on a semiconductor substrate such as silicon which has p-type doping characteristics. Using well-known doping techniques, two spaced-apart diffusion regions are formed on the substrate having n-type characteristics. These diffusion regions are formed on the surface of the substrate and are diffused into the substrate to a depth of generally from about one to about two micrometers, and the diffused regions are spaced about twenty micrometers apart. One of these diffused regions is an electrical source and the other diffused region is an electrical drain in the field-effect transistor to be manufactured.

The area of the semiconductor substrate between the two diffusion regions defines an electrically conducting channel. An electrical insulating layer is placed adjacent the upper surface of the semiconductor substrate except on portions of the diffusion regions which are in direct contact with electrical leads that conduct current from the diffusion regions. These leads comprise an electrically conductive material such as aluminum, n-type silicon and the like. The electrically insulating material may preferably be silicon dioxide, silicon nitride or a silicon dioxide/silicon nitride mixture although alternative materials would be obvious to those skilled in the art. This material is typically thermally grown or otherwise deposited on the surface of the substrate.

The surface region of the substrate located between the two diffusion regions is referred to as the "gate region." The insulator material between the two diffusion regions is known as "gate insulator."

A fugitive layer having a controlled layer thickness is then deposited onto the electrically insulating material. The layer contains a material selected from the group of aluminum and silicon such as the oxide glasses of silicon. This layer, in the area over the gate region will be subsequently removed to provide the gap necessary to obtain a suspended gate field-effect transistor. For this reason, the thickness of the fugitive layer is closely controlled, and is generally between about 0.05 micrometer and about 0.5 micrometer.

It is not desirable to deposit a noble metal gate material onto the fugitive layer as the adhesion between the noble metal and the fugitive layer is weak due to the presence of unstable oxide compounds and/or intermetallic phases and poor bonding thereto. For this reason, a thin film is first deposited on the fugitive layer which forms a stable bond with the fugitive layer and with the noble metal to be subsequently deposited thereon. Materials suitable for incorporation into this thin film that exhibit the necessary bond stability include refractory metals and transition metals and mixtures thereof. Preferably the thin film comprises a mixture of tungsten and titanium. In one preferred embodiment of the invention this thin film comprises a mixture of from about 60 to about 90 atomic weight percent tungsten and from about 10 to about 30 atomic weight percent titanium, based on the total weight of the thin film. This thin film has a thickness of between about 0.05 and 0.10 micrometers.

The noble metal suspended gate material is next deposited onto the thin film layer. Spaced-apart holes are ion-milled or otherwise formed through the noble metal layer and the thin film in the space between the two diffusion regions defining the gate region. An etch solution is inserted into these holes which removes the fugitive layer thereunder and also partially removes the thin film layer. Examples of such etching solutions are known to those skilled in the art such as those listed by W. Kern and C. A. Deckert in "Thin Film Processes", Chapter V-1, Academic Press, 1978, pg. 401, which include phosphoric acid, acetic acid and nitric acid solutions. Preferably the etching occurs at 53–55 degrees C. in a stirred solution of 100 ml $H_2O$, 1600 ml phosphoric acid, 100 ml nitric acid and 100 ml acetic acid diluted 1:25 with water for 1.5 hours.

After removal of the fugitive layer, the noble metal layer is seen to be a gridded suspended gate separated from the gate insulator thereunder by a spacing about equal to the thickness of the fugitive layer. The perforations in the suspended gate permit liquids and gases from the surrounding environment to enter the gate region and affect the electrical response of the field effect transistor based on the chemical sensitivity of the suspended gate to components in the gate region.

A voltage source is connected to the suspended gate and acts to impose an electrical charge on the suspended gate. Another voltage source is connected between the drain and source so as to impose an electrical potential therebetween. An ammeter is included in the circuitry so as to detect and measure the drain current.

To produce suspended gate field-effect transistors having uniform and reproducible sensitivities to gases, it has been found that the noble metal suspended gate must not have any contaminant metal from the prior processing steps remaining thereon. Therefore in accordance with this disclosure, the field-effect transistor is subjected to a further etch, in addition to the acid-etch solution described above, in a buffered etching solution containing a complexing agent for aqueous metal ions and/or metal oxoanions. This etching solution is buffered to maintain the pH in the range of from about 5 to about 11. Preferably the pH is maintained in the range of from about 10.2 to about 10.6, and most preferably is kept at about 10.4. The etching solution is selected for its ability to remove the thin film on which the noble gate metal is deposited without additionally etching the noble metal, fugitive or insulating layers.

One example of such an etching solution is a solution comprising about 0.1 molar ethylenediaminetetraacetic acid (EDTA), 30% hydrogen peroxide and concentrated ammonium hydroxide in a volume ratio of about 5:1.5:1. Such an etching solution is intended to be used at room temperature for a period of time of from about 1 minute to about 30 minutes, preferably about 10 minutes. If the etching solution is in contact with the field effect transistor too long, in excess of about 30 minutes, the solution will begin to unnecessarily etch the the fugitive layer. Also, if the etching solution is permitted to exceed a pH of about greater than 11, the fugitive layer will additionally corrode.

Buffered etching solutions that are suitable for use in this application include those comprising: hydrogen peroxide as the oxidant, EDTA and other carboxylates, bipyridines, phenanthrolines, macrocyclic amines, crown ethers, xanthates, dithiocarbamates, beta-diketonates and their substituted derivatives as complexing agents for metal ions and/or oxoanions; and ammonium hydroxide, sodium hydroxide and potassium hydroxide to establish and maintain the pH of the solution. After this etching process, the suspended gate is seen to consist essentially of noble metal gate material.

In the operation of such a suspended gate field-effect transistor the liquid or gaseous fluid to be analyzed is introduced into the gap region through the gridded suspended gate. Those fluid components that are adsorbed at the surfaces will modify the electric field within the gate region. The change in the electric field is detected within the conducting channel, causing the current flow between the source and drain to be either enhanced or impeded. Any change in the current flow between the drain and source is detected and measured by the ammeter. This measured change in current flow provides a means for calculating the concentration of the fluid component adsorbed by the chemically sensitive field effect transistor.

The above etch step, used to cleanse the suspended gate of any contaminant metals that may be present thereon from prior processing steps, may also be used to regenerate suspended gate field-effect transistors that have been exposed to environments wherein contaminants in the environment were deleteriously deposited on the suspended gate.

BRIEF DESCRIPTION OF THE DRAWINGS

The invention will be further described with reference to the accompanying drawings wherein: FIGS. 1A–E are cross-sectional views of the formation of a chemically sensitive, suspended gate field-effect transistor in accordance with the present invention.

DETAILED DESCRIPTION OF THE DRAWINGS

Figure 1A:
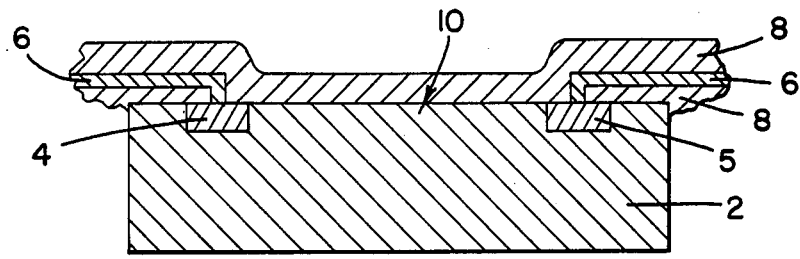

With reference to the figures, the same elements in each figure are represented by the same reference numerals. In referring to the figures, reference will be made to a suspended gate field-effect transistor having a platinum suspended gate and sensitive to the presence of hydrogen in the gate region, an aluminum fugitive layer, and a tungsten/titanium thin film, such limitations are not to be intended to be restrictive of the invention.

With reference to FIG. 1A there is shown therein a silicon substrate 2 having p-type polarity and two spaced apart and doped diffusion regions 4 and 5 having n-type polarity. One of the n-type diffusion regions is referred to as the source, shown as 4 in FIG. 1 and the second is referred to as the drain shown as 5 in the figures. An electrically conductive material 6 such as aluminum is deposited on the source and drain regions 4 and 5 respectively to provide external electrical contacts with the diffusion regions. An insulating material 8, such as silicon dioxide, is disposed around the electrically conductive material 6 and also covers the substrate 2. The region between the two diffusion regions is known as the gate region 10 and is generally referred to in the Figures by arrow 10.

Figure 1B:
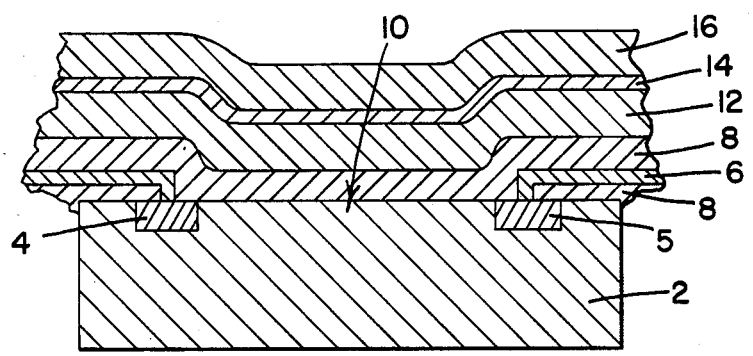

Referring to FIG. 1B there is shown deposited onto the insulator layer 8 a first layer of a fugitive material, aluminum, 12; a thin film comprising tungsten/titanium 14; and a layer of platinum gate material 16. The thickness of the fugitive aluminum layer, especially above the gate region 10, is preferably from about 0.1 to about 0.2 micrometer and most preferably about 0.1 micrometer. The thin film of tungsten/titanium is generally on the order of about 0.05 micrometer thick. The noble metal gate material is deposited onto the thin film and has a thickness ranging from about 0.1 to about 0.4 micrometer.

These three metallic layers may be formed by known deposition processes such as vapor deposition, electroplating, and sputtering.

Figure 1C:
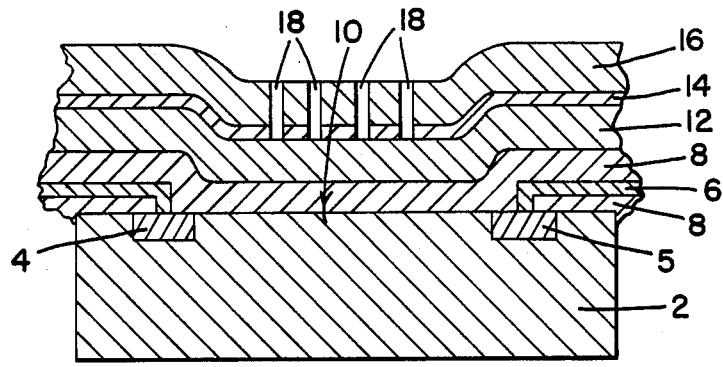

FIG. 1C depicts holes 18 tunneled through the platinum metal layer 16 and tungsten/titanium thin film 14. Typically, these holes are made by ion-milling, but other known techniques such as wet and dry etching may be used with success. The holes are preferably bored through layers 16 and 14 over the gate region 10 of the field effect transistor in a gridded pattern. Typically the size of such holes are on the order of about five micrometers in diameter.

Once the holes have been formed in the noble metal layer 16 and thin film layer 14 an etching solution is disposed into the holes to remove the aluminum found thereunder in fugitive layer 12, as depicted in FIG. 1D. As is shown in this Figure, the etching solution, such as a phosphoric acid etching solution erodes away the aluminum layer 12 and partially erodes away the tungsten/titanium thin film layer 14 in the area around and below the holes 18. After etching there is left an open gate region 20 between the insulating layer 8 and the suspended noble metal gate 16. In accordance with the present invention the tungsten/titanium thin film which is not completely etched from the underside of the noble metal gate layer 16 may interfere with the ability of a chemically sensitive field effect transistor to detect the intended gas, such as hydrogen, with repeated accuracy, and interferes with the uniformity of response among the SGFETs made in this manner.

Therefore, an additional etch is performed to completely remove the thin film layer 14 from the underside of the platinum suspended gate layer 16. This is accomplished with a buffered etching solution containing an oxidizing agent and a complexing agent for metal ions, such as the EDTA-hydrogen peroxide-ammonium hydroxide solution discussed above.

The finally-formed suspended gate, chemically sensitive, field effect transistor is depicted in FIG. 1E. As is also shown in this Figure, the suspended gate 16 is coupled to the substrate by a voltage source 22 that develops a desired reference voltage. A second voltage source 24 is also electrically connected between the electrically conductive leads 6 and 7 so as to establish a potential difference between the source 4 and the drain 5. This potential difference should be of a magnitude sufficient to cause a small but measureable current flow in a conducting channel 28 that comprises that portion of the semiconductor substrate 2 extending between the source and drain diffusion regions 4 and 5, respectively. An ammeter 26 may also be coupled in the circuit between the voltage source 24 and the drain region 5 in order to detect and measure the magnitude of the current flow in conducting channel 28.

The operation and method of chemical detection in such a suspended gate field-effect transistor is fully disclosed in U.S. Pat. No. 4,411,741 to Janata which is incorporated herein by reference.

As taught herein, the suspended gate material must be essentially free from all other metals used to form the field-effect transistor so as to allow substantial uniformity between each so formed field effect transistor and to ensure reproduceability among individual field-effect transistors.

It is to be understood that the foregoing discussion pertaining to the drawings has been provided to enable those skilled in the art to have a representative example by which to evaluate the invention and that limitations imposed on the drawings should not be construed as a restriction on the scope of this invention. It is believed that any of the variables disclosed herein can readily be determined and controlled without departing from the spirit of the invention herein disclosed and described. Moreover, the scope of the invention shall include all modifications and variations that fall within the scope of the attached claims.

I claim:

1. A method of forming a chemically sensitive field-effect transistor having a suspended gate comprising:
    forming in a p-type silicon substrate two spaced-apart diffusion regions of n-type doping polarity;
    connecting an external electrical contact to each of said diffusion regions;
    depositing an electrically insulating layer on the substrate and overlying said electrical contacts and the area between them;
    depositing a fugitive layer containing a material selected from the group consisting of aluminum and silicon on the electrically insulating layer overlying at least the area between said diffusion regions;
    forming a thin film on the fugitive layer overlying at least the area between said diffusion regions, said thin film containing at least one element selected from the group consisting of refractory and transition metals;
    depositing a noble metal gate material on the thin-film overlying at least the area between said diffusion regions;
    removing the fugitive layer from the area between said diffusion regions; and
    etching with a buffered solution containing a complexing agent for metal ions and metal oxoanions to remove any residual portion of the thin film remaining between said diffusion regions after removal of the fugitive layer to form a suspended gate field-effect transistor having noble metal gate material substantially free of said thin film.

2. The method of claim 1 including depositing said fugitive layer to a thickness ranging from about 0.05 micrometer to about 0.5 micrometer.

3. The method of claim 1 including depositing aluminum as said fugitive layer.

4. The method of claim 1 including depositing said thin film to a thickness ranging from about 0.05 micrometer to about 0.10 micrometer.

5. The method of claim 1 including depositing a mixture of tungsten and titanium as said thin film.

6. The method of claim 5 including depositing as said thin film a mixture including about 60 to about 90 atomic weight percent tungsten and from about 10 to about 30 atomic weight percent titanium.

7. The method of claim 1 including depositing platinum as said noble metal gate material.

8. The method of claim 1 including etching with said buffered solution having a pH ranging from about 5 to about 11.

9. The method of claim 1 including etching with said buffered solution having a pH ranging from about 10.2 to about 10.6.

10. The method of claim 1 including maintaining said buffered solution at a pH of about 10.4.

11. The method of claim 1 including selecting said complexing agent from the group consisting of ethylenediaminetetraacetic acid and other carboxylates, bipyridines, phenanthrolines, macrocyclic amines, crown ethers, xanthates, dithiocarbamates, beta-diketonates, and their substituted derivatives.

12. The method of claim 1 including etching with a buffered solution comprising ethylenediaminetetraacetic acid, hydrogen peroxide, and ammonium hydroxide in a volume ratio of about 5:1.5:1.

13. A method of regenerating a chemically sensitive field-effect transistor having a suspended gate comprising disposing said suspended gate in contact with a buffered solution containing a complexing agent for metal ions so as to remove any metal contaminants adhering to said suspended gate.

14. The method of claim 13 including contacting said gate with a buffered solution having a pH ranging from about 5 to about 11.

15. The method of claim 13 including contacting said gate with a buffered solution having a pH ranging from about 10.2 to about 10.6.

16. The method of claim 13 including maintaining said buffered solution at a pH of about 10.4.

17. The method of claim 13 including selecting said complexing agent from the group consisting of ethylenediaminetetraacetic acid, carboxylates, bipyridines, phenanthrolines, macrocyclic amines, crown ethers, xanthates, dithiocarbamates, beta-diketonates and their substituted derivatives.

18. The method of claim 13 including contacting said gate with a buffered solution comprising ethylenediaminetetraacetic acid, hydrogen peroxide and ammonium hydroxide in a volume ratio of about 5:1.5:1.

* * * * *